(12) United States Patent
Bürger et al.

(10) Patent No.: US 8,513,256 B2
(45) Date of Patent: Aug. 20, 2013

(54) SALT FORMS OF 4-(4-METHYLPIPERAZIN-1-YLMETHYL)-N-[4-METHYL-3-(4-PYRIDIN-3-YL)PYRIMIDIN-2-YLAMINO)PHENYL]-BENZAMIDE

(75) Inventors: Hans Michael Bürger, Allschwil (CH); Paul William Manley, Arlesheim (CH); Michael Mutz, Freiburg i. Br. (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/368,811

(22) Filed: Feb. 8, 2012

(65) Prior Publication Data

US 2012/0142697 A1 Jun. 7, 2012

Related U.S. Application Data

(63) Continuation of application No. 10/597,287, filed as application No. PCT/EP2005/001077 on Feb. 3, 2005, now abandoned.

(60) Provisional application No. 60/541,817, filed on Feb. 4, 2004.

(51) Int. Cl.
  *A61K 31/497* (2006.01)
  *A61K 31/505* (2006.01)
  *C07D 403/14* (2006.01)
  *C07D 239/02* (2006.01)
  *C07D 401/14* (2006.01)

(52) U.S. Cl.
  USPC ...... 514/252.18; 514/275; 544/295; 544/322; 544/330; 544/331

(58) Field of Classification Search
  USPC ................... 514/275, 252.18; 544/322, 330, 544/331, 295
  See application file for complete search history.

(56) References Cited

U.S. PATENT DOCUMENTS

| 5,521,184 | A | 5/1996 | Zimmermann et al. |
| 6,448,293 | B1 | 9/2002 | Andrews et al. |
| 6,479,692 | B1 | 11/2002 | Ekwuribe et al. |
| 7,893,076 | B2 | 2/2011 | Mutz |
| 2004/0048899 | A1 | 3/2004 | Choudary et al. |

FOREIGN PATENT DOCUMENTS

| EP | 0 564 409 | 10/1993 |
| WO | WO 99/03854 | 1/1999 |
| WO | WO 02/22597 | 3/2002 |
| WO | WO 03/066613 | 8/2003 |
| WO | WO 03/077892 | 9/2003 |
| WO | WO 2004/074502 | 9/2004 |

OTHER PUBLICATIONS

Berge et al., "Pharmaceutical Salts", Journal of Pharmaceutical Sciences, vol. 66, No. 1, pp. 1-19, Jan. 1977.

*Primary Examiner* — James O Wilson
*Assistant Examiner* — Ebenezer O Sackey
(74) *Attorney, Agent, or Firm* — Stephen Johnson

(57) ABSTRACT

The present invention relates to acid addition salts of 4-[(4-methyl-1-piperazinyl)methyl]-N-[4-methyl-3-[[4-(3-pyridinyl)-2-pyrimidinyl]amino]phenyl]-benzamide, which are selected from the group consisting of a tartrate salt, such as a (D)(−) tartrate salt or a (L)(+) tartrate salt, a hydrochloride salt, a citrate salt, a malate salt, a fumarate salt, a succinate salt, a benzoate salt, a benzenesulfonate salt, a pamoate salt, a formate salt, a malonate salt, a 1,5-naphthalenedisulfonate salt, a salicylate salt, a cyclohexanesulfamate salt, a lactate salt, a mandelate salt, aq glutarate salt, an adipate salt, a squarate salt, a vanillate salt, an oxaloacetate salt, an ascorbate salt and a sulfate salt.

4 Claims, No Drawings

SALT FORMS OF 4-(4-METHYLPIPERAZIN-1-YLMETHYL)-N-[4-METHYL-3-(4-PYRIDIN-3-YL)PYRIMIDIN-2-YLAMINO)PHENYL]-BENZAMIDE

This application is a continuation of U.S. application Ser. No. 10/597,287, which is a 371 of PCT/EP05/001077, filed on Feb. 3, 2005, which claims benefit of U.S. Provisional Application No. 60/541,817, filed on Feb. 4, 2004, which in their entirety are herein incorporated by reference.

The present invention relates to salts forms of the pharmaceutically active compound 4-[(4-methyl-1-piperazinyl)methyl]-N-[4-methyl-3-[[4-(3-pyridinyl)-2-pyrimidinyl]amino]phenyl]-benzamide.

The pharmaceutically active compound 4-[(4-methyl-1-piperazinyl)methyl]-N-[4-methyl-3-[[4-(3-pyridinyl)-2-pyrimidinyl]amino]phenyl]-benzamide is commonly known by its INN name imatinib. Imatinib and its preparation are described in U.S. Pat. No. 5,521,184.

Basic pharmaceutically active compounds are commonly formulated into pharmaceutical preparations as an acid addition salt form, particularly as a crystalline acid addition salt. For example, imatinib is marketed in many countries as its monomethanesulfonate salt (imatinib mesylate) under the brandname GLIVEC or GLEEVEC. Two crystal forms of imatinib mesylate are described in WO 99/03854. The crystal form designated as the beta form is described as having physical properties that make it advantageous for the manufacture of solid oral pharmaceutical dosage forms, such as tablet and capsule dosage forms.

Although it is known that the preparation of salt forms may improve the physical or pharmaceutical properties of a basic pharmaceutically active compound, it is not possible to predict which salt forms may possess advantages for a particular purpose prior to the actual preparation and characterization of the salt form. The present invention relates to salt forms of imatinib, other than imatinib mesylate, that are useful for the manufacture of solid or liquid pharmaceutical dosage forms, particularly solid oral dosage forms, such as tablets and capsules, and liquid oral dosage forms, such as orally administered solutions and suspensions, as well as suppositories and other pharmaceutical dosage forms. Each of these salt forms possesses one or more properties that provides advantages when used as a pharmaceutical active ingredient, such as physical properties that make it easier to manufacture one or more dosage forms, improved stability, improved bioavailability and other such properties that are known to one of skill in the art.

The salt forms of imatinib are prepared by methods known in the art for making acid addition salts of amines, e.g., by treatment of imatinib with an acid or a suitable anion exchange reagent. Typically, imatinib or a solution of imatinib is combined with a solution of an organic or mineral acid in, e.g., a lower alcohol, such as methanol or ethanol, with or without heating. The salt is isolated by crystallization or by evaporation of the solvent and, if desired, purified by re-crystallization from an appropriate re-crystallization solvent by methods known to one of skill in the art.

For the purpose of administering a salt of 4-[(4-methyl-1-piperazinyl)methyl]-N-[4-methyl-3-[[4-(3-pyridinyl)-2-pyrimidinyl]amino]phenyl]-benzamide by means of an oral solution, in general those salts are preferred having an increased water solubility compared to the free base. Salts having a lower water solubility compared to the free base, render them in general more suitable for the manufacture of sustained release formulations compared to the free base.

Important embodiments of this invention include salts of 4-[(4-methyl-1-piperazinyl)methyl]-N-[4-methyl-3-[[4-(3-pyridinyl)-2-pyrimidinyl]amino]phenyl]-benzamide selected from the group consisting of a tartrate salt, such as a (D)(−) tartrate salt or a (L)(+) tartrate salt, a hydrochloride salt, a citrate salt, a malate salt, particularly a D-malate salt, a fumarate salt, a succinate salt, a benzoate salt, a benzenesulfonate salt, a pamoate salt, a formate salt, a malonate salt, a 1,5-naphthalenedisulfonate salt, a salicylate salt, a cyclohexanesulfamate salt, a lactate salt, particularly a (S)-lactate salt, a mandelate salt, particularly an (R)(−) mandelate salt, a glutarate salt, an adipate salt, a squarate salt, a vanillate salt, an oxaloacetate salt, an ascorbate salt, particularly an (L)-ascorbate salt and a sulfate salt.

Further important embodiments of this invention include imatinib ascorbate, imatinib formate, imatinib malonate, imatinib oxaloacetate, imatinib squarate and imatinib vanillate.

In a preferred embodiment of the present invention, the acid addition salt is selected from the group consisting of a tartrate salt, such as a (D)(−) tartrate salt or a (L)(+) tartrate salt, a hydrochloride salt, a citrate salt, a malate salt, particularly a D-malate salt, a fumarate salt, a succinate salt, a benzoate salt, a benzenesulfonate salt, a pamoate salt, a hemiformate salt, a malonate salt, a salicylate salt, a cyclohexanesulfamate salt, a mandelate salt, particularly an (R)(−) mandelate salt, a hemiglutarate salt, an adipate salt, a vanillate salt and a sulfate salt.

In a further preferred embodiment of the present invention, the acid addition salt is selected from the group consisting of imatinib D-tartrate, imatinib D-malate, imatinib hemiformate, imatinib malonate, imatinib salicylate, imatinib hemiglutamate, imatinib cyclohexanesulfamate, imatinib mandelate, particularly imatinib (R)(−) mandelate, imatinib adipate, imatinib vanillate and imatinib sulfate.

The present invention further relates to a pharmaceutical composition comprising one of the above mentioned salts of imatinib and a pharmaceutically acceptable carrier.

In one embodiment, the invention relates to a pharmaceutical composition which comprises a pharmaceutically acceptable carrier and an acid addition salt of 4-[(4-methyl-1-piperazinyl)methyl]-N-[4-methyl-3-[[4-(3-pyridinyl)-2-pyrimidinyl]amino]phenyl]-benzamide selected from the group consisting of a tartrate salt, such as a (D)(−) tartrate salt or a (L)(+) tartrate salt, a hydrochloride salt, a citrate salt, a malate salt, particularly a D-malate salt, a fumarate salt, a succinate salt, a benzoate salt, a benzenesulfonate salt, a pamoate salt, a formate salt, a malonate salt, a 1,5-naphthalenedisulfonate salt, a salicylate salt, a cyclohexanesulfamate salt, a lactate salt, particularly a (S)-lactate salt, a mandelate salt, particularly an (R)(−) mandelate salt, aq glutarate salt, an adipate salt, a squarate salt, a vanillate salt, an oxaloacetate salt, an ascorbate salt, particularly an (L)-ascorbate salt and a sulfate salt.

In an important embodiment, the acid addition salt is selected from the group consisting of imatinib ascorbate, imatinib formate, imatinib malonate, imatinib oxaloacetate, imatinib squarate and imatinib vanillate.

The invention relates also to a process for the treatment of warm-blooded animals suffering from a tumour disease, wherein a quantity of one of acid addition salt of 4-[(4-methyl-1-piperazinyl)methyl]-N-[4-methyl-3-[[4-(3-pyridinyl)-2-pyrimidinyl]amino]phenyl]-benzamide disclosed herein which is effective against the disease concerned, especially a quantity with antiproliferative and especially tumour-inhibiting efficacy, is administered to warm-blooded animals in need of such treatment, especially the treatment of gliomas, ovarian tumours, prostate tumours, gastro-intestinal stromal tumors, colon tumours, and tumours of the lung, such as especially small cell lung carcinoma, and tumours of the breast or other gynaecological tumours and, in particular leukemia. Depending on species, age, individual condition, mode of administration, and the clinical picture in question, effective doses, for example daily doses of about 10-2000 mg, preferably 25-1000 mg, especially 50-800 mg, are administered to warm-blooded animals of about 70 kg bodyweight.

In a further aspect, the present invention relates to the use of an acid addition salt of 4-[(4-methyl-1-piperazinyl)methyl]-N-[4-methyl-3-[[4-(3-pyridinyl)-2-pyrimidinyl]amino]phenyl]-benzamide according to any one claims 1 to 4 for the manufacture of a pharmaceutical composition for the treatment of a tumour disease, especially the treatment of gliomas, ovarian tumours, prostate tumours, gastro-intestinal stromal tumors, colon tumours, and tumours of the lung, such as especially small cell lung carcinoma, and tumours of the breast or other gynaecological tumours and, in particular leukemia.

The following Examples illustrate the invention without limiting the scope thereof.

EXAMPLE 1

4-[(4-Methyl-1-piperazinyl)methyl]-N-[4-methyl-3-[[4-(3-pyridinyl)-2-pyrimidinyl]amino]phenyl]-benzamide, tartrate 4-[(4-Methyl-1-piperazinyl)methyl]-N-[4-methyl-3-[[4-(3-pyridinyl)-2-pyrimidinyl]amino]phenyl]-benzamide (4.94 g, 10 mmol) is added to a solution of (2R,3R)-2,3-dihydrorybutanedioic acid (L-(+)-tartaric acid; Fluka, Buchs, Switzerland; 1.50 g, 10 mmol) in hot ethanol (40 mL). The solution is evaporated to dryness under reduced pressure and the resulting residue is re-crystallized from methanol to afford, after filtering and drying, 4-[(4-methyl-1-piperazinyl)methyl]-N-[4-methyl-3-[[4-(3-pyridinyl)-2-pyrimidinyl]amino]phenyl]-benzamide, tartrate as a pale-yellow crystalline solid, having the following analytical properties: Analysis found: C, 60.18; H, 5.96; N, 14.86%; $H_2O$, 2.25%. Calculated for $C_{33}H_{37}N_7O_7$-0.82 $H_2O$: C, 60.19; H, 5.91; N, 14.89%. $H_2O$, 2.24%.

EXAMPLE 2

4-[(4-Methyl-1-piperazinyl)methyl]-N-[4-methyl-3-[[4-(3-pyridinyl)-2-pyrimidinyl]amino]phenyl]benzamide, hydrochloride Aqueous hydrochloric acid (0.99 g of 37%) is added to a solution of 4-[(4-methyl-1-piperazinyl)methyl]-N-[4-methyl-3-[[4-(3-pyridinyl)-2-pyrimidinyl]amino]phenyl]benzamide (4.94 g, 10 mmol) in ethanol (20 mL). The solution is evaporated to dryness under reduced pressure and the resulting residue is re-crystallized from ethanol-ethylacetate. The product is filtered-off and re-crystallized from isopropanol to afford, after filtering and drying, 4-[(4-methyl-1-piperazinyl)methyl]-N-[4-methyl-3-[[4-(3-pyridinyl)-2-pyrimidinyl]amino]phenyl]-benzamide, hydrochloride as a pale-yellow crystalline solid, having the following analytical properties: Analysis found: C, 65.27; H, 6.07; N, 18.19; Cl, 6.55%; $H_2O$, 0.56%. Calculated for $C_{29}H_{32}N_7OCl$-0.17 $H_2O$: C, 65.33; H, 6.11; N, 18.39; Cl, 6.65%; $H_2O$, 0.57%.

EXAMPLE 3

4-[(4-Methyl-1-piperazinyl)methyl]-N-[4-methyl-3-[[4-(3-pyridnyl)-2-pyrimidinyl]amino]phenyl]-benzamide, citrate 4-[(4-Methyl-1-piperazinyl)methyl]-N-[4-methyl-3-[[4-(3-pyridinyl)-2-pyrimidinyl]amino]phenyl]-benzamide (4.94 g, 10 mmol) is added to a solution of anhydrous 2-hydroxy-1,2,3-propanetricarboxylic acid (citric acid; Merck, Darmstadt, BRD; 1.92 g, 10 mmol) in methanol (30 mL) at room temperature. Upon cooling, 4-[(4-methyl-1-piperazinyl)methyl]-N-[4-methyl-3-[[4-(3-pyridinyl)-2-pyrimidinyl]amino]phenyl]-benzamide, citrate crystallizes and is filtered and dried to afford a pale-yellow crystalline solid, having the following analytical properties: Analysis found: C, 59.24; H, 5.71; N, 13.60%, $H_2O$, 2.14%. Calculated for $C_{35}H_{39}N_7O_8$-0.83 $H_2O$: C, 60.00; H, 5.85; N, 13.99%; $H_2O$, 2.13%.

EXAMPLE 4

4-[(4-Methyl-1-piperazinyl)methyl]-N-[4-methyl-3-[[4-(3-pyridinyl)-2-pyrimidinyl]amino]phenyl]-benzamide, malate 4-[(4-Methyl-1-piperazinyl)methyl]-N-[4-methyl-3-[[4-(3-pyridinyl)-2-pyrimidinyl]amino]phenyl]-benzamide (4.94 g, 10 mmol) is added to a solution of (2S)-(−)-hydroxybutanedioic acid (L-(−)-malic acid; Fluka, Buchs, Switzerland; 1.34 g, 10 mmol) in water (40 mL). The mixture is heated and the resulting hot solution is filtered and evaporated to dryness under reduced pressure to give a residue which is re-crystallized from ethanol, filtered and dried to give 4-[(4-methyl-1-piperazinyl)methyl]-N-[4-methyl-3-[[4-(3-pyridinyl)-2-pyrimidinyl]amino]phenyl]benzamide, malate as a pale-yellow crystalline solid, having the following analytical properties: Analysis found: C, 62.88; H, 6.04; N, 15.60%; $H_2O$, 0.45%. Calculated for $C_{33}H_{37}N_7O_6$-0.16 $H_2O$: C, 62.86; H, 5.97; N, 15.55%; $H_2O$, 0.46%.

EXAMPLE 5

4-[(4-Methyl-1-piperazinyl)methyl]-N-[4-methyl-3-[[4-(3-pyridinyl)-2pyrimidinyl]amino]phenyl]-benzamide, fumarate (Trans)-butenedioic acid (fumaric acid; Fluka, Buchs, Switzerland; 1.16 g, 10 mmol) is added to a solution of 4-[(4-methyl-1-piperazinyl)methyl]-N-[4-methyl-3-[[4-(3-pyridinyl)-2-pyrimidinyl]amino]phenyl]benzamide (4.94 g, 10 mmol) in ethanol (25 mL). The mixture is heated to 90° C., treated with water (18 g) and filtered. Upon cooling, the product crystallizes and is filtered and dried to afford 4-[(4-methyl-1-piperazinyl)methyl]-N-[4-methyl-3-[[4-(3-pyridinyl)-2-pyrimidinyl]amino]phenyl]-benzamide, fumarate a pale-yellow crystalline solid, having the following analytical properties: Analysis found: C, 63.91; H, 5.99; N, 15.74%; $H_2O$, 1.27%. Calculated for $C_{33}H_{35}N_7O_5$-0.44 $H_2O$: C, 64.18; H, 5.86; N, 15.88%; $H_2O$, 1.28%.

EXAMPLE 6

4-[(4-Methyl-1-piperazinyl)methyl]-N-[4-methyl-3-[[4-(3-pyridinyl)-2-pyrimidinyl]amino]phenyl]-benzamide, succinate 4-[(4-Methyl-1-piperazinyl)methyl]-N-[4-methyl-3-[[4-(3-pyridinyl)-2-pyrimidinyl]amino]phenyl]benzamide (4.94 g, 10 mmol) is added to a solution of butanedioic acid (succinic acid; Fluka, Buchs, Switzerland; 1.18 g, 10 mmol) is added to a solution of in ethanol (25 mL). The mixture is heated to 90° C., treated with water (0.2 g) and filtered. Upon cooling, the product crystallizes and is filtered and dried to afford 4-[(4-methyl-1-piperazinyl)methyl]-N-[4-methyl-3-

[[4-(3-pyridinyl)-2-pyrimidinyl]amino]phenyl]-benzamide, succinate as a pale-yellow crystalline solid, having the following analytical properties: Analysis found: C, 64.19; H, 6.11; N, 15.82%; $H_2O$, 0.87%. Calculated for $C_{33}H_{37}N_7O_5$-0.30 $H_2O$: C, 64.23; H, 6.14; N, 15.89%; $H_2O$, 0.88%.

EXAMPLE 7

4-[(4-Methyl-1-piperazinyl)methyl]-N-[4-methyl-3-[[4-(3-pyridinyl)-2-pyrimidinyl]amino]phenyl]benzamide, benzoate 4-[(4-Methyl-1-piperazinyl)methyl]-N-[4-methyl-3-[[4-(3-pyridinyl)-2-pyrimidinyl]amino]phenyl]-benzamide (4.94 g, 10 mmol) is added to a solution of benzoic acid (Fluka, Buchs, Switzerland; 1.22 g, 10 mmol) in xylene (50 mL). The mixture is heated and the resulting hot solution is filtered. Upon cooling, the product crystallizes and is filtered and dried to afford 4-[(4-methyl-1-piperazinyl)methyl]-N-[4-methyl-3-[[4-(3-pyridinyl)-2-pyrimidinyl]amino]phenyl]-benzamide, benzoate as a pale-brown crystalline solid, having the following analytical properties: Analysis found: C, 70.13; H, 6.12; N, 16.24%. Calculated for $C_{36}H_{37}O_3$: C, 70.22; H, 6.06; N, 15.92%.

EXAMPLE 9

4-[(4-Methyl-1-piperazinyl)methyl]-N-[4-methyl-3-[[4-(3-pyridinyl)-2-pyrimidinyl]amino]phenyl]-benzamide, benzenesulphonate 4-[(4-Methyl-1-piperazinyl)methyl]-N-[4-methyl-3-[[4-(3-pyridinyl)-2-pyrimidinyl]amino]phenyl]-benzamide (4.94 g, 10 mmol) is added to a solution of benzenesulphonic acid (Fluka, Buchs, Switzerland; 1.61 g, 10 mmol) in hot toluene (40 mL). The solution is evaporated to dryness under reduced pressure and the resulting residue is re-crystallized from ethanol-ethylacetate. The product is filtered-off and dried to afford 4-[(4-methyl-1-piperazinyl)methyl]-N-[4-methyl-3-[[4-(3-pyridinyl)-2-pyrimidinyl]amino]phenyl]-benzamide, benzenesulphonate as a pale-yellow crystalline solid, having the following analytical properties: Analysis found: C, 64.19; H, 5.68; N, 14.93; S, 4.87%; $H_2O$, 0.34%. Calculated for $C_{35}H_{37}N_7O_4S$-0.12 $H_2O$: C, 64.28; H, 5.74; N, 14.99; S, 4.90%; $H_2O$, 0.33%.

EXAMPLE 10

4-[(4-Methyl-1-piperazinyl)methyl]-N-[4-methyl-3-[[4-(3-pyridinyl)-2-pyrimidinyl]amino]phenyl]-benzamide, pamoate A mixture of 4-[(4-methyl-1-piperazinyl)methyl]-N-[4-methyl-3-[[4-(3-pyridinyl)-2-pyrimidinyl]amino]phenyl]-benzamide (4.94 g, 10 mmol) and 4,4'-methylenebis[3-hydroxy-2-naphthoic acid (Fluka, Buchs, Switzerland; 3.88 g, 10 mmol) in ethanol (50 mL) is heated. Water (25 mL) is then added. Upon cooling, the product crystallises and is filtered-off and dried to afford 4-[(4-methyl-1-piperazinyl)methyl]-N-4-methyl-3-[[4-(3-pyridinyl)-2-pyrimidinyl]amino]phenyl]-benzamide, pamoate as a pale-yellow solid, having the following analytical properties: Analysis found: C, 69.12; H, 5.62; N, 10.88%; $H_2O$, 2.50%. Calculated for $C_{52}H_{47}N_7O_7$-1.26 $H_2O$: C, 69.04; H, 5.52; N, 10.84%; $H_2O$, 2.51%.

EXAMPLE 11

4-[(4-Methyl-1-piperazinyl)methyl]-N-[4-methyl-3-[[4-(3-pyridinyl)-2-pyrimidinyl]amino]phenyl]benzamide, salicylate A solution of 2-hydroxybenzoic acid (salicylic acid; Fluka, Buchs, Switzerland; 558 mg, 4 mmol) in ethanol (50 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is reduced in volume to 80 mL by rotary evaporation at 90° C. and 400 mbar and then slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, salicylate as a crystalline solid, having the following analytical properties: Analysis found: C, 68.18; H, 5.93; N, 15.52; O, 10.42%. $H_2O$, 0.31%. Calculated for $C_{36}H_{37}N_7O_4$-0.11 $H_2O$: C, 68.23; H, 5.92; N, 15.47; O, 10.38%. $H_2O$, 0.31%.

EXAMPLE 12

4-[(4-Methyl-1-piperazinyl)methyl]-N-[4-methyl-3-[[4-(3-pyridinyl)-2-pyrimidinyl]amino]phenyl]-benzamide vanillate A solution of 4-hydroxy-3-methoxybenzoic acid (vanillic acid; Fluka, Buchs, Switzerland; 694 mg, 4 mmol) in ethanol (50 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The solution is evaporated to dryness under reduced pressure and the resulting residue is re-crystallized from ethanol-acetone. The product is filtered-off and dried to afford 4-[(4-methyl-1-piperazinyl)methyl]-N-[4-methyl-3-[[4-(3-pyridinyl)-2-pyrimidinyl]amino]phenyl]-benzamide, vanillate as a crystalline solid, having the following analytical properties: Analysis found: C, 66.61; H, 6.18; N, 14.74; 0, 12.86%. $H_2O$, 0.84%. Calculated for $C_{37}H_{39}N_7O_5$-0.31 $H_2O$: C, 66.59; H, 5.98; N, 14.69; O, 12.73%. $H_2O$, 0.84%.

EXAMPLE 13

4-[(4-Methyl-1-piperazinyl)methyl]-N-[4-methyl-3-[[4-(3-pyridinyl)-2-pyrimidinyl]amino]phenyl]-benzamide, cyclohexanesulphamate A solution of N-cyclohexylsulphamic acid (Fluka, Buchs, Switzerland; 732 mg, 4 mmol) in ethanol (100 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The solution is evaporated to dryness under reduced pressure and the resulting residue is re-crystallized from ethanol-isopropanol. The product is filtered-off and dried to afford 4-[(4-methyl-1-piperazinyl)methyl]-N-[4-methyl-3-[[4-(3-pyridinyl)-2-pyrimidinyl]amino]phenyl]-benzamide, sulphamate as a crystalline solid, having the following analytical properties: Analysis found: C, 61.13; H, 6.75; N, 15.87; O, 11.80; S, 4.57%. $H_2O$, 1.69%. Calculated for $C_{35}H_{44z}N_8O_4S$-0.40 i-PrOH-0.70 $H_2O$: C, 61.28; H, 6.90; N, 15.79; O, 11.50; S, 4.52%. $H_2O$, 1.78%.

EXAMPLE 14

4-[(4-Methyl-1-piperazinyl)methyl]-N-[4-methyl-3-[[4-(3-pyridinyl)-2-pyrimidinyl]amino]phenyl]-benzamide, hemiglutarate A solution of 1,5-pentanedioic acid (glutaric acid; Fluka, Buchs, Switzerland; 539 mg, 4 mmol) in ethanol (60 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is reduced in volume to 80 mL by rotary evaporation at 90° C. and 400 mbar and then slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]benzamide, hemiglutarate as a crystalline solid, having the following analytical properties: Analysis found: C, 64.62; H, 5.81; N, 16.81; O, 11.96%. $H_2O$, 4.14%. Calculated for $C_{32}H_{36}N_7O_3 \cdot 1.5\ H_2O$: C, 64.74; H, 6.62; N, 16.51; O, 12.13%. $H_2O$, 4.55%.

EXAMPLE 15

4-[(4-Methyl-1-piperazinyl)methyl]-N-[4-methyl-3-[[4-(3-pyridinyl)-2-pyrimidinyl]amino]phenyl]benzamide, malonate A solution of 1,3-propanedioic acid (malonic acid; Fluka, Buchs, Switzerland; 420.5 mg, 4 mmol) in ethanol (60 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, malonate as a crystalline solid, having the following analytical properties: Analysis found: C, 64.0; H, 6.1; N, 16.3; O, 13.6%. $H_2O$, <0.3%. Calculated for $C_{32}H_{35}N_7O_5$: C, 64.31; H, 5.90; N, 16.40; O, 13.38%.

EXAMPLE 16

4-[(4-Methyl-1-piperazinyl)methyl]-N-[4-methyl-3-[[4-(3-pyridinyl)-2-pyrimidinyl]amino]phenyl]benzamide, sulphate A solution of sulphuric acid (Fluka, Buchs, Switzerland; 4.0 mL of 1 M) in ethanol (50 mL) is added to a solution of 4-[(4-methyl-1-piperazinyl)methyl]-N-[4-methyl-3-[[4-(3-pyridinyl)-2-pyrimidinyl]amino]phenyl]benzamide (1.975 g, 4 mmol) in hot ethanol (350 mL at 90° C.). The hot solution is slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, sulphate as a crystalline solid, having the following analytical properties: Analysis found: C, 55.17; H, 5.82; N, 15.57; O, 18.29; S, 5.26%. $H_2O$, 5.89%. Calculated for $C_{29}H_{33}N_7O_5S \cdot 2.06\ H_2O$: C, 55.34; H, 5.95; N, 15.59; O, 17.96; S, 5.10%. $H_2O$, 5.90%.

EXAMPLE 17

4-[(4-Methyl-1-piperazinyl)methyl]-N-[4-methyl-3-[[4-(3-pyridinyl)-2-pyrimidnyl]amino]phenyl]-benzamide, adipate A solution of 1,6-hexanedioic acid (adipic acid; Fluka, Buchs, Switzerland; 1081 mg, 4 mmol) in ethanol (80 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is reduced in volume to 80 mL by rotary evaporation at 90° C. and 400 mbar and then slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, adipate as a crystalline solid, having the following analytical properties: Analysis found: C, 64.97; H, 6.33; N, 15.44; O, 12.77%. $H_2O$, 1.43%. Calculated for $C_{35}H_{41}N_7O_5 \cdot 0.5\ H_2O$: C, 64.76; H, 6.53; N, 15.10; O, 13.61%. $H_2O$, 1.44%.

EXAMPLE 18

4-[(4-Methyl-1-piperazinyl)methyl]-N-[4-methyl-3-[[4-(3-pyridinyl)-2-pyrimidinyl]amino]phenyl]benzamide, (R)-(−)-mandelate A solution of (R)-(−)-alpha-hydroxybenzeneaceticlic acid ((D)-(−)-mandelic acid; Fluka, Buchs, Switzerland; 553 mg, 3.13 mmol) in ethanol (60 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is reduced in volume to 80 mL by rotary evaporation at 90° C. and 400 mbar and then slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, mandelate as a crystalline solid, having the following analytical properties: Analysis found: C, 68.60; H, 6.27; N, 15.19; O, 9.91%. $H_2O$, 0.22%. Calculated for $C_{37}H_{39}N_7O_4 \cdot 0.08\ H_2O$: C, 68.67; H, 6.10; N, 15.15; O, 10.09%. $H_2O$, 0.22%.

EXAMPLE 19

4-[(4-Methyl-1-piperazinyl)methyl]-N-[4-methyl-3-[[4-(3-pyridinyl)-2-pyrimidinyl]amino]phenyl]-benzamide, malate A solution of (2R)-(−)-hydroxybutanedioic acid ((D)-malic acid; Fluka, Buchs, Switzerland; 553 mg, 2.83 mmol) in ethanol (60 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is reduced in volume to 80 mL by rotary evaporation at 90° C. and 400 mbar and then slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, malate as a crystalline solid, having the following analytical properties: Analysis found: C, 62.14; H, 6.33; N, 15.48; O, 16.18%. $H_2O$, 1.99%. Calculated for $C_{33}H_{37}N_7O_6 \cdot 0.71\ H_2O$: C, 61.88; H, 6.05; N, 15.31; O, 16.76%. $H_2O$, 2.00%.

EXAMPLE 20

4-[(4-Methyl-1-piperazinyl)methyl]-N-[4-methyl-3-[[4-(3-pyridinyl)-2-pyrimidinyl]amino]phenyl]-benzamide, (D)-(−)-tartrate A solution of (2S,3S)-2,3-dihydroxy-butanedioic acid (tartaric acid; Fluka, Buchs, Switzerland; 606.5 mg, 1.97 mmol) in ethanol (90 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The hot solution is slowly cooled to 20° C. to afford, after filtering and drying, 4-[(4-methyl-1-piperazinyl)methyl]-N-[4-methyl-3-[[4-(3-pyridinyl)-2-pyrimidinyl]amino]phenyl]-benzamide, tartrate as a crystalline solid, having the following analytical properties: Analysis found: C, 60.54; H, 6.08; N, 14.37; O, 18.89%. $H_2O$, 1.32%. Calculated for $C_{33}H_{37}N_7O_7$-0.50 EtOH-0.50 $H_2O$: C, 60.43; H, 6.12; N, 14.51; O, 18.94%. $H_2O$, 1.33%.

EXAMPLE 21

4-[(4-Methyl-1-piperazinyl)methyl]-N-[4-methyl-3-[[4-(3-pyridinyl)-2-pyrimidinyl]amino]phenyl]benzamide, hemiformate A solution of formic acid (Fluka, Buchs, Switzerland; 368 mg, 8 mmol) in ethanol (20 mL) is added to a solution of 4-[(4-methyl-1-piperazinyl)methyl]-N-[4-methyl-3-[[4-(3-pyridinyl)-2-pyrimidinyl]amino]phenyl]-benzamide (1.975 g, 4 mmol) in hot ethanol (150 mL at 90° C.). The solution is evaporated to dryness under reduced pressure and the resulting residue is re-crystallized from acetone. The product is filtered-off and dried to afford 4-[(4-methyl-1-piperazinyl)methyl]-N-[4-methyl-3-[[4-(3-pyridinyl)-2-pyrimidinyl]amino]phenyl]-benzamide, hemiformate as a crystalline solid, having the following analytical properties: Analysis found: C, 68.50; H, 6.24; N, 18.93; O, 6.43%. $H_2O$, 1.69%. Calculated for $C_{59}H_{64}N_{14}O_4$-1.80 $H_2O$: C, 68.46; H, 6.25; N, 18.95; O, 6.34%. $H_2O$, 0.17%.

EXAMPLE 22

Capsules

Capsules containing 100 mg of a 4-[(4-methyl-1-piperazinyl)methyl]-N-[4-methyl-3-[[4-(3-pyridinyl)-2-pyrimidinyl]amino]phenyl]-benzamide salt ("Salt") are usually prepared in the following composition:

Composition

| | |
|---|---|
| Salt | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

EXAMPLE 23

Water Solubility

Solubility in water at room temperature of the 4-[(4-methyl-1-piperazinyl)methyl]-N-[4-methyl-3-[[4-(3-pyridinyl)-2-pyrimidinyl]amino]phenyl]benzamide salts is as listed in Table 1 below. For comparison, the solubility of the free base in water at room temperature is 0.44 mg/ml.

TABLE 1

| Salt of Example | Solubility in water at room temperature in mg/ml |
|---|---|
| 1 | >51 |
| 2 | 32.5 |
| 3 | 38.2 |
| 4 | >49 |
| 5 | 9.71 |
| 6 | 50.1 |
| 7 | 47.9 |
| 8 | 47 |
| 9 | >44 |
| 10 | 0.32 |
| 15 | >53 |

The invention claimed is:

1. An acid addition salt of 4-[(4-methyl-1-piperazinyl)methyl]-N-[4-methyl-3-[[4-(3-pyridinyl)-2-pyrimidinyl]amino]phenyl]-benzamide (Imatinib) selected from the group consisting of a (D)(−) tartrate salt, a (L)(+) tartrate salt, succinate salt, and a malonate salt.

2. An acid addition salt according to claim 1 selected from the group consisting of imatnib, D-tartrate and imatinib malonate.

3. A pharmaceutical composition which comprises a pharmaceutically acceptable carrier and an acid addition salt of 4-[(4-methyl-1-piperazinyl)methyl]-N-[4-methyl-3-[[4-(3-pyridinyl)-2-pyrimidinyl]amino]phenyl]-benzamide (Imatinib) selected from the group consisting of a tartrate salt, a (D)(−) tartrate salt, a (L)(+) tartrate salt, a succinate salt, and a malonate salt.

4. A method for treating leukemia in a patient in need thereof comprising the step of administering a therapeutically effective amount of an acid addition salt of 4-[4-methyl-1-piperazinyl)methyl]-N-[4-methyl-3-[[4-(3-pyridinyl)-2-pyrimidinyl]amino]phenyl]-benzamide according to claim 1 or 3.

* * * * *